United States Patent
Yokosuka et al.

(10) Patent No.: US 10,290,464 B2
(45) Date of Patent: May 14, 2019

(54) CHARGED PARTICLE BEAM DEVICE AND PATTERN MEASUREMENT DEVICE

(71) Applicant: Hitachi High-Technologies Corporation, Minato-ku, Tokyo (JP)

(72) Inventors: Toshiyuki Yokosuka, Tokyo (JP); Chahn Lee, Tokyo (JP); Hideyuki Kazumi, Tokyo (JP); Manabu Hasegawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/759,408

(22) PCT Filed: Aug. 15, 2016

(86) PCT No.: PCT/JP2016/073035
§ 371 (c)(1),
(2) Date: Mar. 12, 2018

(87) PCT Pub. No.: WO2017/051621
PCT Pub. Date: Mar. 30, 2017

(65) Prior Publication Data
US 2018/0182595 A1  Jun. 28, 2018

(30) Foreign Application Priority Data

Sep. 25, 2015 (JP) ................. 2015-187591

(51) Int. Cl.
*H01J 37/28* (2006.01)
*H01J 37/22* (2006.01)
(Continued)

(52) U.S. Cl.
CPC .............. *H01J 37/28* (2013.01); *G01B 15/00* (2013.01); *G01B 15/04* (2013.01); *G01N 23/22* (2013.01);
(Continued)

(58) Field of Classification Search
CPC .......... H01J 37/28; H01J 37/22; H01J 37/222; H01J 37/244; G01B 15/00; G01B 15/04;
(Continued)

(56) References Cited

U.S. PATENT DOCUMENTS 8,356,260 B2  1/2013 Nagatomo et al.
8,586,921 B2  11/2013 Boughorbel et al.
(Continued)

FOREIGN PATENT DOCUMENTS

JP  2001-272219 A  10/2001
JP  2006-64421 A   3/2006
(Continued)

OTHER PUBLICATIONS

International Search Report (PCT/ISA/210) issued in PCT Application No. PCT/JP2016/073035 dated Nov. 15, 2016 with English-language translation (five (5) pages).
(Continued)

*Primary Examiner* — Nicole M Ippolito
(74) *Attorney, Agent, or Firm* — Crowell & Moring LLP (57) ABSTRACT

The present invention provides a charged particle beam device capable of predicting the three-dimensional structure of a sample, without affecting the charge of the sample. The present invention provides a charged particle beam device characterized in that a first distance between the peak and the bottom of a first signal waveform obtained on the basis of irradiation with a charged particle beam having a first landing energy, and a second distance between the peak and the bottom of a second signal waveform obtained on the basis of irradiation with a charged particle beam having a second landing energy different from the first landing energy are obtained, and the distance between the peak and the bottom at a landing energy (zero, for instance) different from the first and second landing energies is obtained on the basis
(Continued)

of the extrapolation of the first distance and the second distance.

12 Claims, 10 Drawing Sheets

(51) Int. Cl.
*H01J 37/244* (2006.01)
*G01N 23/22* (2018.01)
*G03F 7/20* (2006.01)
*G01B 15/00* (2006.01)
*G01B 15/04* (2006.01)
*G01N 23/2251* (2018.01)

(52) U.S. Cl.
CPC ..... *G01N 23/2251* (2013.01); *G03F 7/70625* (2013.01); *H01J 37/22* (2013.01); *H01J 37/222* (2013.01); *H01J 37/244* (2013.01)

(58) Field of Classification Search
CPC . G01N 23/22; G01N 23/2251; G03F 7/70625
USPC ............ 250/306, 307, 309, 310, 311, 492.1, 250/492.2, 492.21, 492.22, 492.23, 492.3
See application file for complete search history.

(56) References Cited

U.S. PATENT DOCUMENTS

| | | | |
|---|---|---|---|
| 9,202,665 B2* | 12/2015 | Matsui | H01J 37/026 |
| 2006/0043292 A1 | 3/2006 | Matsui | |
| 2007/0187595 A1* | 8/2007 | Tanaka | G01N 23/2251 |
| | | | 250/307 |
| 2012/0138796 A1* | 6/2012 | Sasajima | H01J 37/222 |
| | | | 250/311 |
| 2015/0357158 A1* | 12/2015 | Suzuki | H01J 37/30 |
| | | | 250/307 |
| 2016/0379798 A1 | 12/2016 | Shishido et al. | |

FOREIGN PATENT DOCUMENTS

| | | |
|---|---|---|
| JP | 2007-227618 A | 9/2007 |
| JP | 2013-219031 A | 10/2013 |
| JP | 2015-106530 A | 6/2015 |

OTHER PUBLICATIONS

Japanese-language Written Opinion (PCT/ISA/237) issued in PCT Application No. PCT/JP2016/073035 dated Nov. 15, 2016 (four (4) pages).

* cited by examiner

CROSS-SECTIONAL VIEW OF PATTERN

ELECTRON MICROSCOPE IMAGE

Fig. 13

CHARGED PARTICLE BEAM DEVICE AND PATTERN MEASUREMENT DEVICE

TECHNICAL FIELD

The present invention relates to a charged particle beam device and a pattern measurement device, and more particularly to a charged particle beam device and a pattern measurement device for executing pattern measurement based on a plurality of signals obtained by a scanning with beams under different conditions.

BACKGROUND ART

With miniaturization mid three-dimensional structuring of a semiconductor pattern, a slight difference in shape affects an operation characteristic of a device, and shape management needs are increasing. For that reason, high sensitivity and high precision are increasingly required in the seaming electron microscope (SEM) used for inspection, and measurement of semiconductors.

In order to accurately ascertain a shape of the pattern, a method of measuring a three-dimensional shape of the pattern is known. In PTL 1, a method of estimating a taper inclination by acquiring a secondary electron image and a backscattered electron image at an observation site, respectively, and per matching with a secondary electron image and a backscattered electron image acquired in a reference pattern is disclosed. In PTL 2, a method of detecting a secondary electron for each emission angle, for each energy, and estimating a structure in a depth direction in order to obtain information in the depth direction is disclosed. In PTL 3, a method of estimating the depth of a pattern from luminance change at the bottom when an acceleration voltage is changed with respect to a deep hole and deep groove material is disclosed. As a method of estimating a cross-sectional shape using the SEM, there is a model-based library (MBL) method. In the MBL method, a cross-sectional shape of a three-dimensional structure is estimated by comparing secondary electron detection signal intensity distribution obtained by scanning a sample with a primary electron beam and secondary electron signal intensity distribution obtained by being calculated in advance for various cross-sectional shapes. Regarding the MBL, description is made in PTL 4, for example.

CITATION LIST

Patent Literature

PTL 1: JP-A-2001-272219
PTL 2: JP-A-2013-219031 (corresponding U.S. Pat. No. 8,586,921)
PTL 3: JP-A-2015-106530
Pit 4: JP-A-2007-227618 (corresponding U.S. Pat. No. 8,356,260)

SUMMARY OF INVENTION

Technical Problem

On the other hand, due to miniaturization of the pattern, it is becoming difficult to accurately ascertain the three-dimensional shape, to accurately specify a pattern portion, and to perform highly accurate measurement of the pattern, and the like. Even if the patterns have temporarily different shapes due to miniaturization, the difference is becoming difficult to recognize on the SEM image. Also, due to the influence of charging or the like, there is a possibility that a position different from the original measurement reference is taken as a measurement target. According to the method disclosed in PTL 1, although the approximate inclination of the taper can be estimated, highly accurate estimation cannot be performed due to the influence of charge adhering to a sample when the sample is irradiated with the electron beam, in some cases. This also applies to PTLs 2, 3, and 4 that acquire waveforms and the like obtained by irradiating the sample with the electron beam.

In the following, a charged particle beam device and a pattern measurement apparatus which have an object to perform highly accurate pattern measurement, pattern identification, and the like, regardless of the influence of charging and the like are proposed.

Solution to Problem

According to an aspect of the present invention in order to achieve the object described above, in the following, there is proposed a charged particle beam device which includes a scanning deflector for the scanning with a charged particle beam emitted from a charged particle source, a detector for detecting the charged particle obtained based on the scanning with the charged particle beam with respect to a sample, and a computation device for generating a signal waveform based on an output of the detector and computing a pattern dimension formed on the sample by using the signal waveform, and in which the computation device calculates an index value relating to a pattern formed on the sample at least from a first measurement result obtained by the scanning with the charged particle beam having first landing energy and a second measurement result obtained by the scanning with the charged particle beam having second landing energy.

The first measurement result and the second measurement result are dimensional values relating to a pattern and an edge dimension value at thud landing energy other than the first landing energy and the second landing energy is calculated by extrapolation. The third landing energy is set to zero, for example.

Furthermore, as another aspect of the present invention for achieving the object described above, there is proposed a pattern measurement device which includes a computation device for generating a signal waveform based on a detection signal obtained by a charged panicle beam device and calculating the dimension of a pattern formed on a sample using the signal waveform, and in which the computation device calculates an index value relating to the pattern formed on the sample at least from a first measurement result obtained by the scanning with the charged particle beam having first landing energy and a second measurement result obtained by the scanning with the charged particle beam having second landing energy.

Advantageous Effects of Invention

According to the configuration described above, it is possible to perform highly accurate pattern measurement, pattern identification, and the like, regardless of the influence of charges or the like.

BRIEF DESCRIPTION OF DRAWINGS

SADP.

DESCRIPTION OF EMBODIMENTS

While higher integration of semiconductor devices are required, there is an increasing demand for three-dimensional structuring of semiconductor devices. In a device having a three-dimensional structure, the number of parts influencing device characteristics such as a taper angle and a shape of a corner portion of a line increases, and there is a need for dimensional management (three-dimensional shape management) different from that of the related art.

A scanning electron microscope (SEM) is a device for detecting electrons and the like emitted from a sample, generates a signal waveform by detecting such electrons, and measures, for example, a dimension between peaks (pattern edges).

Among the electrons emitted from the sample, secondary electrons having low energy are easily influenced by charging of the sample. In recent years, due to miniaturization of patterns and use of low dielectric constant materials such as low-k, the influence of charge becomes obvious. For example, in a case where there is a dielectric around a pattern to be measured, charging may occur by the scanning with the electron beam, and a signal waveform shape may change. That is, highly precise measurement may be difficult due to deformation of the signal waveform caused by charging. A trajectory of the low-energy electron beam is deflected by sample charging, and it may be difficult to cause the beam to land on the desired position.

As described above, due to the influence caused by sample charging, it may be difficult to perform highly accurate measurement, pattern identification using signal waveforms, or to collate with reference information. In the embodiment to be described below, description will be made on a charged particle beam device capable of performing highly accurate pattern measurement, pattern identification, or the like mainly using a plurality of pieces of information of different landing energies of an electron beam (charged particle beam) with respect to a sample, or a pattern measurement device.

Specifically, description will be made on a charged particle beam device which includes, for example, a charged particle source, a deflector that scans a sample with a charged particle beam emitted from the charged particle source, a detector for detecting backscattered electrons, which have a low angle (horizontal direction) and are emitted by the scanning with the charged particle beam with respect to the sample, separately from secondary electrons, an image memory for storing a signal obtained by the scanning with the charged particle beam with respect to the sample, and a computation device for measuring a dimension of the pattern formed on the sample based on irradiation with the charged particle beam, and in which the computation device calculates a first distance between a peak and a bottom of a first signal waveform obtained based on irradiation with the charged particle beam having first landing energy and a second distance between a peak and a bottom of a second sural waveform obtained based on irradiation with the charged particle beam having second landing energy different from the first landing energy, and calculates a distance between the peak and the bottom at landing energy different from the first and second landing energies, based on extrapolation of the first distance and the second distance. According to such a configuration, it is possible to perform three-dimensional structure estimation of the pattern while suppressing the influence of charging, by using the backscattered electrons.

In the embodiment described below, description will be made on a charged particle beam device for estimating a three-dimensional structure of a pattern mainly using backscattered electrons or highly accelerated secondary electrons. The backscattered electrons and highly accelerated secondary electrons can be detected by discrimination detection using an energy filter or a trajectory difference generated when electrons emitted from the sample are deflected. The backscattered electrons or highly accelerated secondary electrons may be collided with a secondary electron conversion electrode and be detected after conversion into secondary electrons.

In the embodiment described below, description will be made on, for example, a charged particle beam device which includes an objective lens for converging a charged particle beam emitted from a charged particle source, a deflector for changing a scanning position of the charged particle beam, a control device for controlling the scanning deflector, a sample stage for mounting a sample, and a detector for separating secondary electrons and backscattered electrons among the charged particles emitted from the sample and detecting only backscattered electrons, and estimates a round width and a taper width at acceleration=0 V based on change in a taper distance and a round distance of the pattern, based on the SEM image obtained from two or more acceleration conditions.

Figure 1:
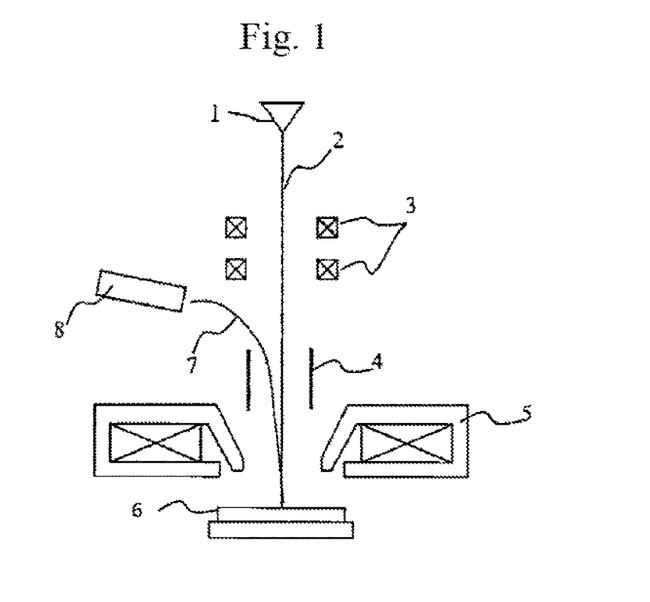
FIG. 1 is a diagram illustrating an outline of a scanning electron microscope.

FIG. 1 illustrates a schematic view of a scanning electron microscope which is a type of charged particle beam device. An electron beam 2 (electron beam) generated by an electron gun 1 is converged by a condenser lens 3 and finally converged on a sample 6 by an objective lens 5. The electron beam 2 is scanned (hereinafter, also referred to as scanning) on the electron beam scanning region of the sample by the deflector 4 (scanning deflector). Primary electrons are two-dimensionally scanned, excited in the sample by irradiation, backscattered electrons 7 and secondary electrons emitted from the sample are detected by the detector 8, and signals of the electrons are converted into an image, thereby performing observation and measurement of the sample. The scanning electron microscope of FIG. 1 is provided with a control device (not illustrated) and the control device controls each optical element of the electron microscope. A negative voltage application power source (not illustrated) is connected to the sample stage for mounting the sample 6 and the control device controls landing energy of the electron beam to the sample by controlling the negative voltage application power source. In the following description, an example in which landing energy of the electron beam is controlled by controlling the voltage applied to the sample will be described, but the present invention is not limited thereto, and landing energy of the electron beam to the sample may be controlled by controlling an acceleration power source connected between an electron source and an acceleration electrode for accelerating the electron beam. The SEM illustrated in FIG. 1 includes an image memory that stores a detection signal for each pixel, and the detection signal is stored in the image memory.

Furthermore, the scanning electron microscope exemplified in FIG. 1 is provided with a computation device (not illustrated). The computation device executes dimension measurement of the pattern based on image data stored in the image memory. More specifically, a profile waveform is formed based on luminance into matron stored for each pixel, and dimension measurement of the pattern is executed based on interval information between one peak and another peak of the profile waveform, or between one peak and the start point of the peak.

In a case where the sample is a dielectric, a two-dimensional charge distribution is formed in a scanning region (FOV) during SEM observation. Since electrons mainly detected by the SEM are secondary electrons having a large amount of emission and small energy (~several eV), the secondary electrons are easily influenced by slight charging formed on the surface. For that reason, in the SEM observation of a charged sample, an obtained image varies depending on what charge distribution is formed at the time of irradiation. As parameters which determine the charge distribution of a surface, in addition to the energy of the primary electrons that influences the emission amount of secondary electrons, an amount of electric current, electron beam scanning order, and scanning speed, and even when an apparatus side is under the same condition, charging changes due to the difference in material characteristics and shape.

Figure 2:
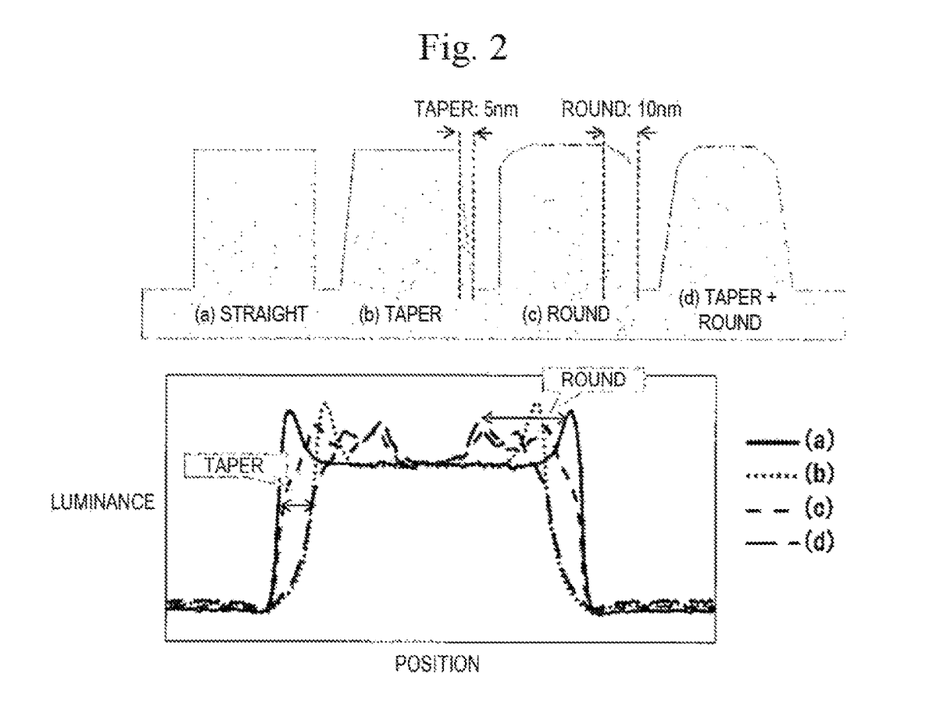
FIG. 2 is a diagram illustrating signal waveforms of backscattered electrons when line patterns having different shapes are scanned.
Figure 3:
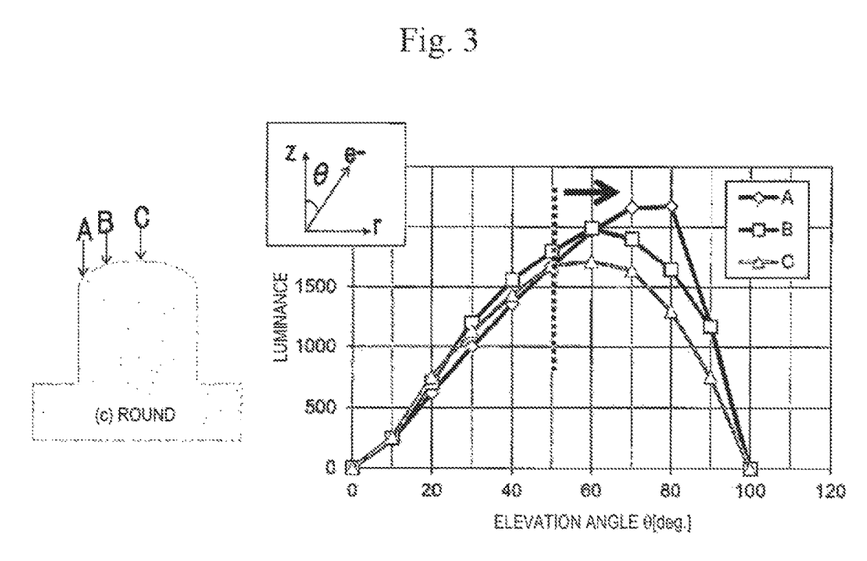
FIG. 3 is a diagram illustrating an angle (elevation angle) distribution of backscattered electrons emitted from a line pattern.

For that reason, it is considered effective to estimate the original shape from an electronic image generated based on emitted electrons having high energy, which is hardly influenced by charging. High energy electrons emitted from the sample are backscattered electrons that primary electrons are scattered inside the sample and are emitted as they are, but since the backscattered electrons are elections scattered in a wide range with respect to the secondary electrons, there is a problem that spatial resolution is low. On the other hand, even when backscattered electrons are obliquely incident onto the pattern, electrons of a specific angle have sensitivity to a shape. For example, FIG. 2 illustrates a result obtained by simulation of a profile of backscattered electrons when four kinds of various line patterns are irradiated with primary electrons. At corner portions (hereinafter, referred to as "edges") of the pattern, the shape of the profile is different, and it can be seen that the shape can be determined. In this case, the angle (elevation angle) distribution of electrons emitted from each place is illustrated in FIG. 3. As a result of plotting the distribution of angles with respect to the optical axis with the vertical direction being 0 degree, it is understood that electrons contributing to the difference in shape are electrons emitted in the horizontal direction having an elevation angle of 50 degrees or more. By detecting these electrons, it is possible to identify the difference in shape. In the case of the taper, deviation of the peak position indicates the presence or absence of the taper, and in the case of the round, spread of the peak indicates the degree of the round. As described above, even in backward scattered electrons, there is shape sensitivity depending on the detected electrons and it is possible to make rough shape determination. On the other hand, the backscattered electrons have a wider scattering range within the sample than the secondary electrons and the peak position of the profile does not become an edge position of the pattern and thus, it is difficult to estimate a pattern structure from the profile of one image.

Figure 4:
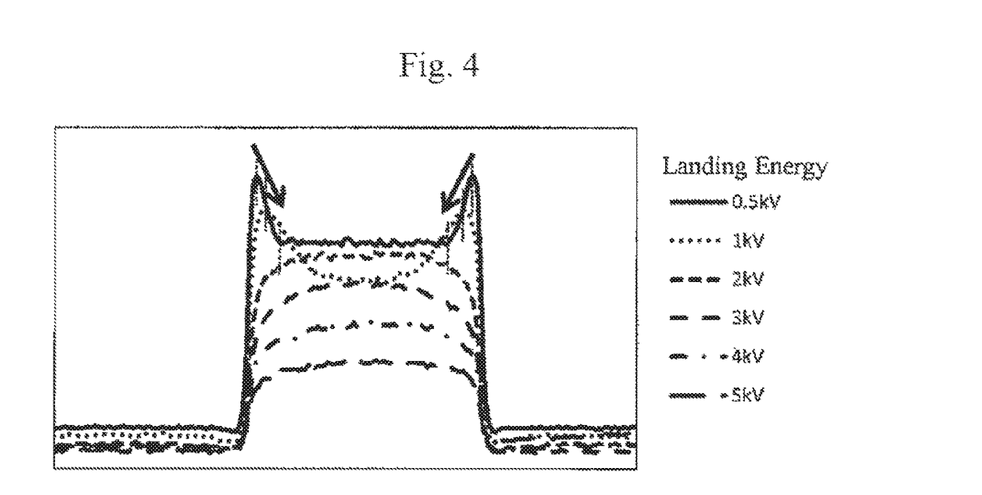
FIG. 4 is a diagram illustrating signal waveforms of backscattered electrons when an acceleration voltage is changed.

For that reason, in the present embodiment, a method of estimating a true edge position from a backscattered electron image acquired under a plurality of acceleration conditions is proposed. FIG. 4 illustrates a profile when the accelerating voltage (landing energy of the primary electron to the sample) is changed with respect to the same pattern. The peak position of the profile changes by changing the acceleration voltage. Since the peak position is determined by a magnitude of primary electron scattered inside the pattern, the peak position moves to the inside of the pattern as acceleration increases (scattering range becomes wider). From this, it can be estimated that the peak position at the state where a scattering range is minimized (landing energy≈0 V) is the edge position of an actual pattern. From the matters described as above, the edge position is obtained by estimating a taper distance from extrapolation of a bottom-to-peak distance of two or more acceleration voltages. The state in which landing energy is 0 V is a state in which there is no scattering in the sample when the electron beam lauds on the sample. That is, since an irradiation position of the electron beam is in the scattering range, an acquired measurement value can be regarded as being acquired in a state where there is no influence of electron beam scattering, under this state. Originally in irradiation with low energy electrons (≈0 V), it is influenced by charging of the sample, but the influence of charging can be eliminated by estimating a dimension value from extrapolation of the measurement result of high energy electrons. According to the method exemplified in the present embodiment, it is possible to acquire information that is not influenced by electron beam irradiation, based on a detection signal obtained by irradiating an electron beam.

Figure 5:
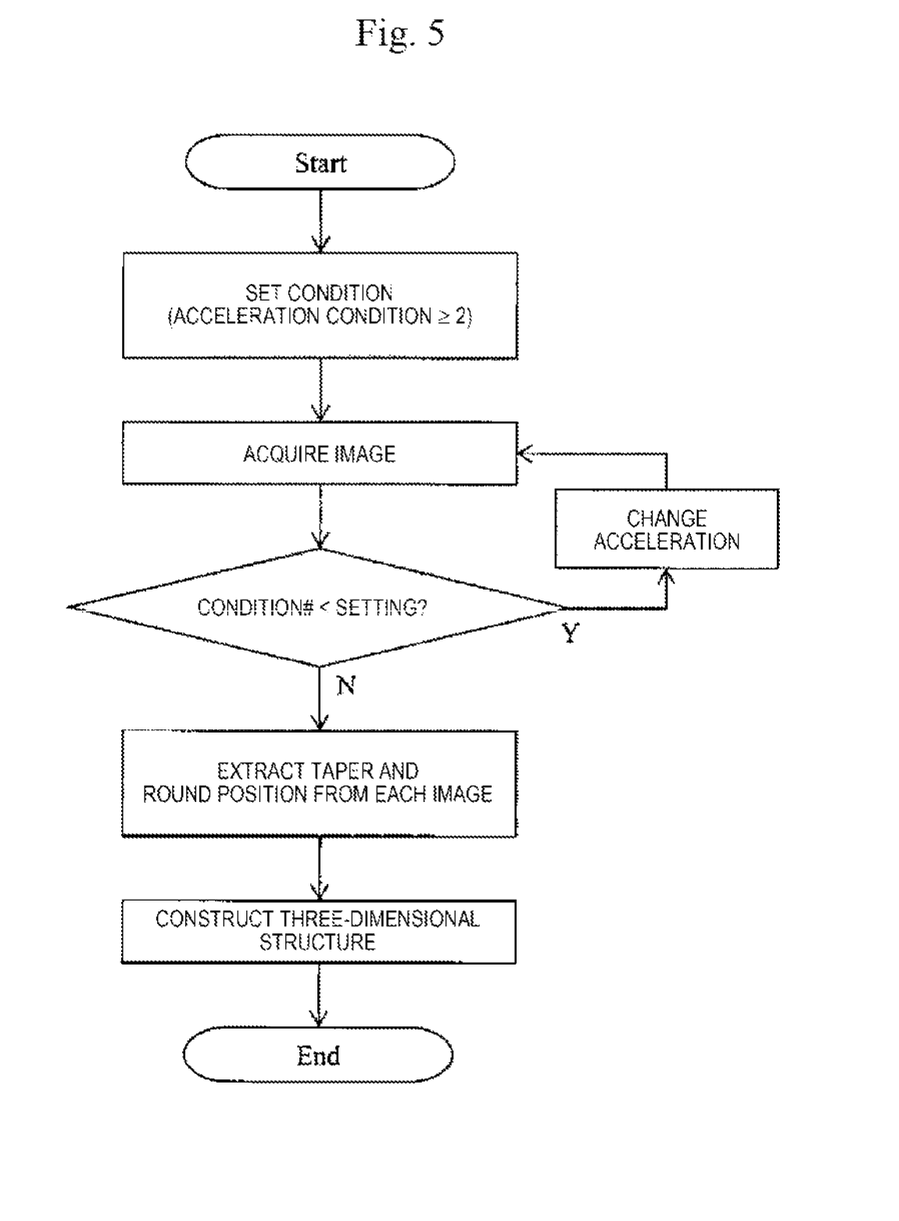
FIG. 5 is a diagram illustrating a flow for extracting a feature quantity of a three-dimensional structure.

FIG. 5 illustrates a flow for extracting a feature quantity according to the present embodiment. First, an acceleration condition for obtaining a backscattered electron image is set. At this time, at least two or more acceleration conditions to be set are set. In a case where an energy filter for discriminating detected electrons by energy of electrons is provided in the front stage of the detector, the energy of the electrons to be detected is set in the energy filter. Next, an image is acquired based on the set conditions. Here, the image can be automatically acquired under the set conditions by being combined with a recipe and the like. If a condition number for which the image is acquired matches the setting condition, processing proceeds to the next step. When there is a condition not yet acquired, the acceleration voltage is changed and image acquisition is performed again. From an obtained backscattered electron image, extraction of the taper position and the round position are performed. Processing to be performed here will be described later. Extrapolation from the obtained taper and round width value for each acceleration is performed and the taper width at acceleration 0 V is estimated (computed). In this case, extrapolation is possible by performing fitting with a linear expression, a polynomial expression or the like, and an operator selects an optimum function. A three-dimensional structure is constructed by using the taper width and round shape obtained at acceleration of 0 V. For information in the depth direction, it may be estimated from brightness of the bottom. For an estimated structure, the operator can display the shape on the GUI, if necessary.

Figure 6A:
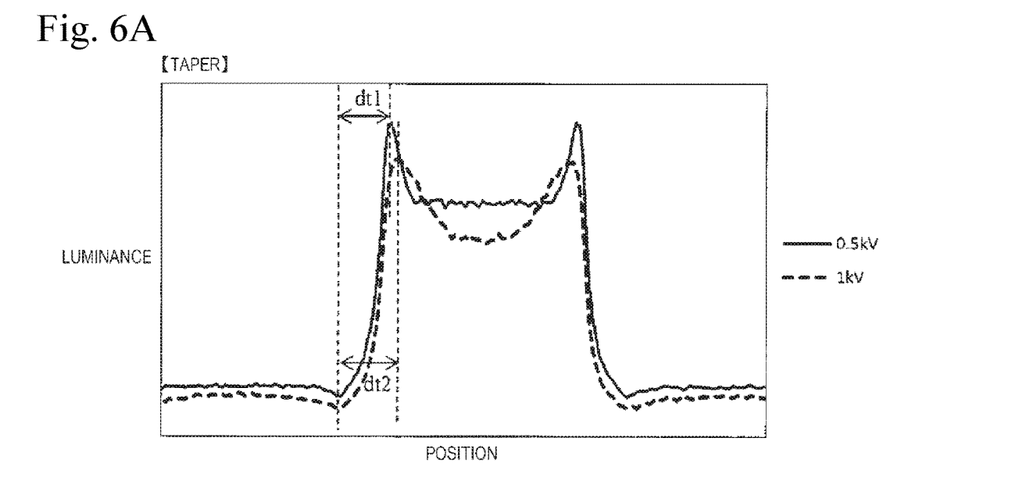
FIGS. 6A and 6B are diagrams illustrating signal waveforms of backward scattered electrons in a taper shaped pattern and derivation of a taper width by extrapolation.
Figure 6B:
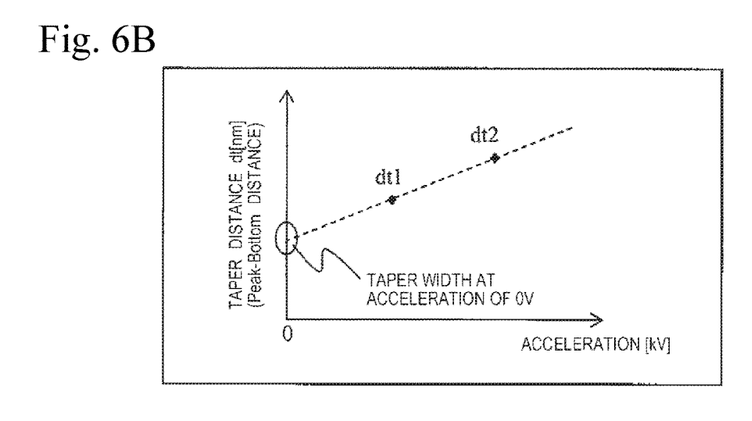

Extraction processing of the taper and round positions will be described below with reference to the drawings. FIG. 6 illustrates a profile of backscattered electrons having the taper shape. Regarding the taper, a distance dt between the bottom position and the peak position is defined as a taper width at each acceleration, the value is obtained for each acceleration (landing energy), and the taper width at acceleration of 0 V is obtained by an extrapolation method (FIG. 6(b)).

Figure 7A:
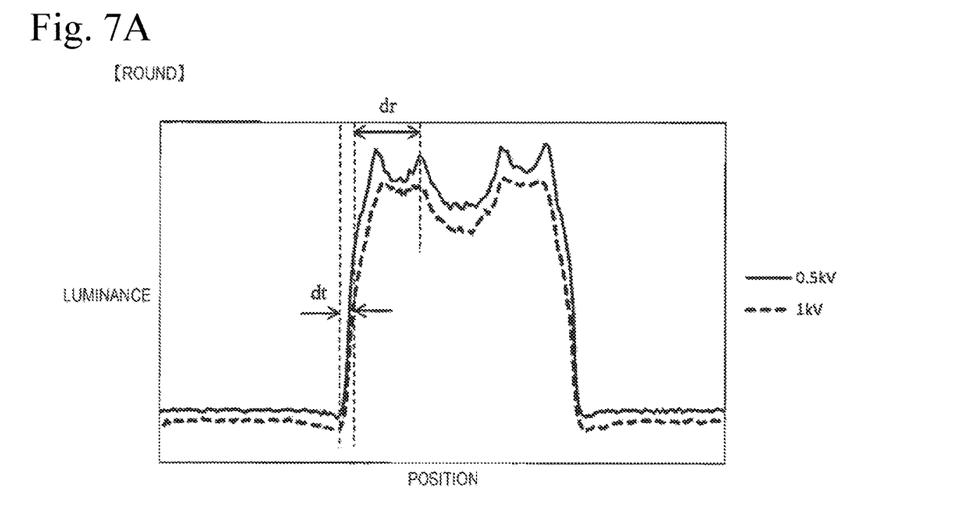
FIGS. 7A and 7B are diagrams illustrating signal waveforms of a backward scattered electron in a round shaped pattern and an inclination of luminance.
Figure 7B:
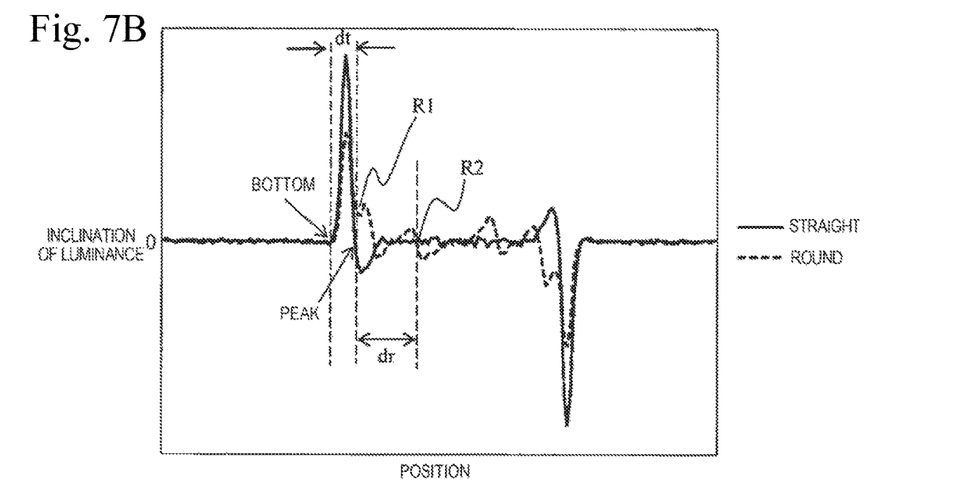

On the other hand, regarding the round shape, it is difficult to distinguish whether a peak appearing first is the result reflecting either the taper or the round. For that reason, separation between the taper and the round is performed based on the inclination (differential value) of luminance. FIG. 7 illustrates (a) a profile of a round shape (no taper) and (b) a differential waveform of luminance. The (b) differential waveform also illustrates the result of a straight shape (a pattern where the edge rises vertically as illustrated in FIG. 2 (a)) for comparison.

Since the waveform of the straight shape exemplified in FIG. 7(b) is a differential waveform, a waveform value of the differential waveform corresponding to the peak top of a luminance signal waveform is zero, and the sign of the waveform value is inverted on the left and right thereof. On the other hand, in the differential waveform having the round shape, a change appears in inclination at a point (position in the X axis direction) R1 where the differential waveform of the straight shape reaches zero. This position is defined as a taper position, and the distance dt from the bottom is obtained for each acceleration.

Since the results in FIG. 7 (b) are the shapes of no taper (zero taper width), the same position as that of the straight shape is derived as R1 (round shape starting point). On the other hand, regarding the round width, a distance dr between R1 and a peak position R2 is obtained for each acceleration. As described above, first, the taper position R1 is estimated and then the round width is obtained when the round shape is predicted. Also, for dt and dr, a value at acceleration of 0 V is derived by extrapolation from the change in value with respect to acceleration.

Figure 8:
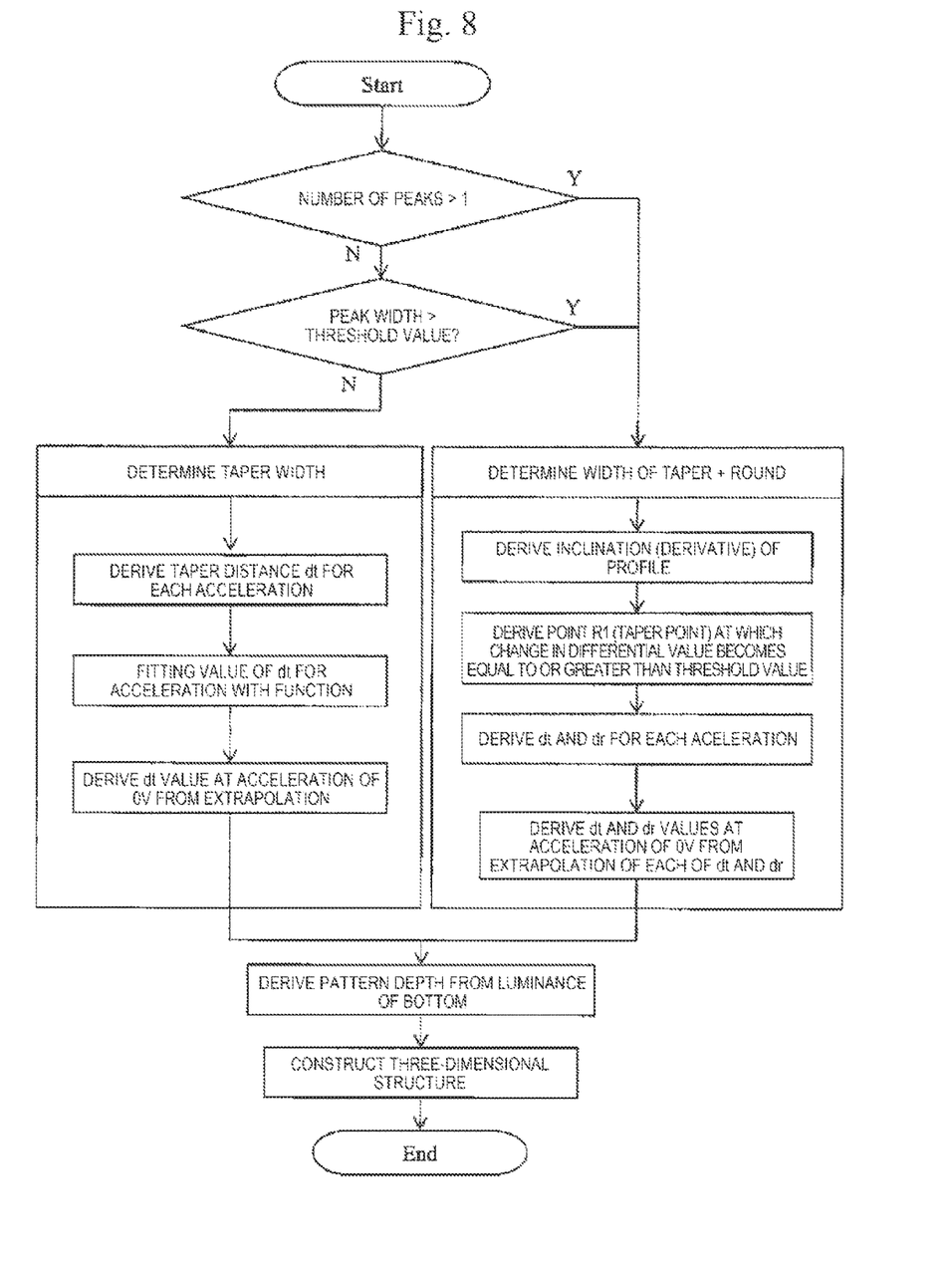
FIG. 8 is a diagram illustrating extraction processing of positions of a taper and a round of a line pattern and a flow of three-dimensional structure construction.

FIG. 8 illustrates a flow of extraction processing of the taper position and the round position and a three-dimensional structure construction. The presence or absence of a round is determined from a profile of the pattern by the umber of peaks and the width of the peak. In a case where there is a round shape, the peak of one side edge is separated or the peak width is increased, as illustrated in the profile illustrated in FIG. 2. Accordingly, it is determined whether there are more than 1 peaks at 1 edge position or not and whether the peak width exceeds a predetermined threshold or not, and in a case where there is no such feature in the profile, processing proceed to determine the taper width assuming that there is no round. As the threshold in determining, it is desirable to ascertain a relationship between the shape and the peak in advance by simulation or the like for the round shape, the peak width, and the like and to set an optimum value according to management needs.

In a determination step of the taper width, the taper width is derived by processing illustrated in FIG. 6. In a case where it is determined that there is a round, a taper point R1 is defined from the profile, values of dt and dr are derived for each acceleration, respectively, and a value at acceleration of 0 V is obtained. The shape obtained as described above reflects a shape in the horizontal direction, and information on the depth direction is necessary to predict the three-dimensional structure. Regarding prediction of depth information, there is a method of deriving the depth from luminance of the bottom of the pattern, and the depth information may be obtained by utilizing this method. More specifically, electrons emitted from the bottom of a deep hole or the like generally become difficult to escape to a surface of the sample as the depth of the hole is deeper, and the deeper the hole, the lower the luminance of the bottom portion, compared with a case of the depth is shallow. Accordingly, it is conceivable to prepare a database that stores the relationship between luminance of the bottom portion and the depth information or a relational expression and to obtain the depth information by referring to luminance of the bottom portion which is actually obtained.

Figure 9:
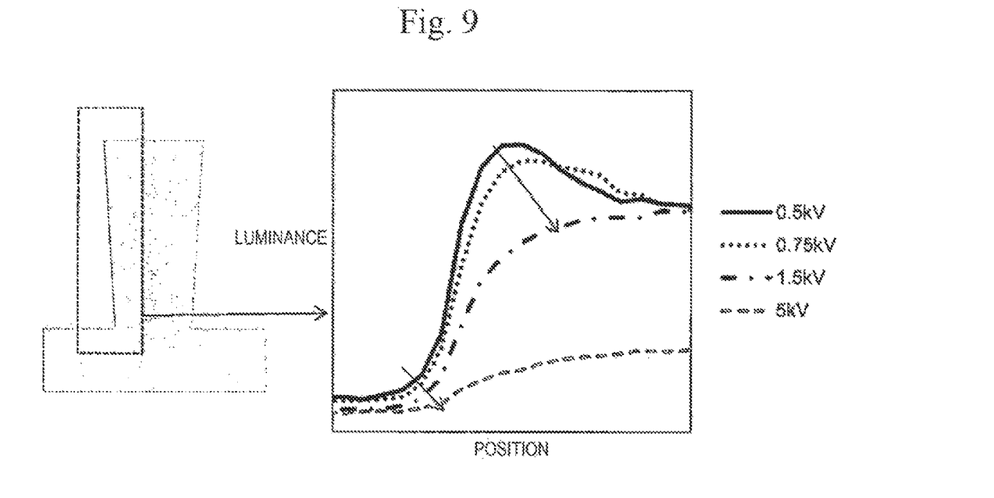
FIG. 9 is a diagram illustrating an example of signal waveforms of backward scattered electrons when a line pattern having a reverse taper is scanned.

A case where this flow is applied to a pattern of a reverse taper structure will be described below with reference to the drawings. FIG. 9 illustrates a pattern having a reverse taper structure and a profile of backscattered electrons. The difference from the forward taper described above is the point where the bottom position changes due to an increase of the acceleration voltage. This is because electrons penetrating through the sample increase due to the increase of the acceleration voltage, and the higher the acceleration, the more the actual bottom position is reflected. If the distance between the bottoms of the patterns is calculated and this distance becomes short due to acceleration voltage increase, it can be determined as the reverse taper pattern. As the acceleration increases, the change in the bottom position converges at a stage when all the electrons penetrate the pattern, and the value at this time becomes the true bottom position. On the other hand, regarding the edge position of the pattern surface, similarly to the forward taper, the position at acceleration of 0 V may be calculated from the peak position which changes due to acceleration.

Figure 12:
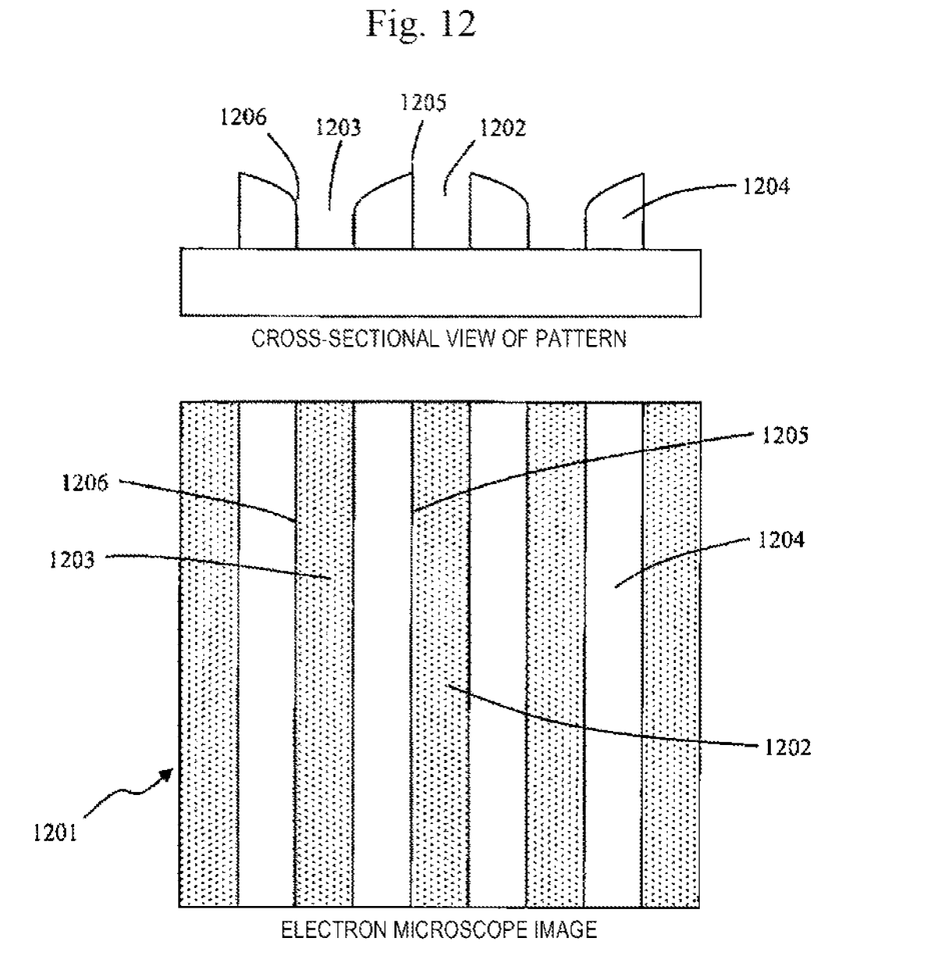
FIG. 12 is a diagram illustrating an example of a pattern generated by SADP.

Next, a processing step of identifying the type of the pattern or extracting the edge to be measured from a plurality of edges based on information obtained by changing the landing energy, instead of determining whether or not it is the reverse taper structure, and executing measurement will be described. FIG. 12 illustrates a cross-sectional view of a pattern formed by a self aligned double patterning (SADP) method and an example of an electron microscope image. According to the SADP method, as illustrated in FIG. 12, a group of patterns in which patterns 1204 of which shapes of the left and right edges are different are alternately changed in orientation is generated. Space sandwiched between steeply rising edges 1205 (edge A) is called a core gap 1202, and space sandwiched between edges 1206 (edge B) consisting of gently inclined surfaces is called a spacer gap 1203. Since the core gap 1202 and the spacer gap 1203 are formed by different manufacturing processes, respectively, in order to accurately perform step management of the semiconductor process, it is necessary to identify both the core gap 1202 and the spacer gap 1203, and to specify the gap generated by the manufacturing process to be evaluated, or an edge adjacent to the gap. However, as illustrated in the lower diagram of FIG. 12, the core gap and the spacer gap may appear to be the same on an electron microscope image 1201, and it may be difficult to identify. Also, since the difference in edge shape may appear as a difference in signal waveform shape, it is conceivable to identify between the core gap and the spacer gap by evaluating the peak shape of the waveform corresponding to the edge, but this difference becomes a slight difference according to miniaturization of patterns, for example, there is also a possibility that determination will be erroneous due to the influence of charging.

Figure 13:
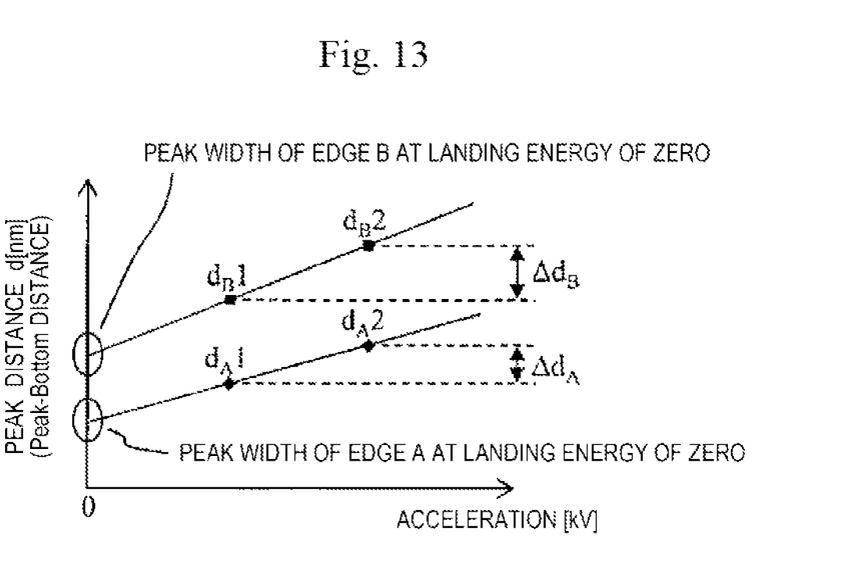
FIG. 13 is a diagram for explaining an example of obtaining an index value relating to a pattern based on a plurality of measurement values obtained by changing landing energy.

In view of such a situation in the present embodiment, identification of an appropriate pattern or specification of an edge to be measured is executed by generating a signal waveform before and after change of the landing energy and obtaining a difference value or the like of the feature quantity (for example, a taper width) of the edge. FIG. 13 is a diagram illustrating an example in which peak widths of the edge 1205 and the edge 1206 are measured twice on the same edge based on irradiation with beams having different landing energies. When the landing energy of the electron beam is V1, the results of measuring the peak widths of the edges 1205 and 1206 are $d_A1$ and $d_B1$, respectively, and when the landing energy of the electron beam is V2, the results of measuring the peak widths of the edges 1205 and 1206 are $d_A2$ and $d_B2$, respectively.

A peak width of the edge 1205 when the landing energy is zero is calculated based on extrapolation using $d_A1$ and $d_A2$ obtained as above, a peak width of the edge 1206 when the landing energy is zero is calculated based on extrapolation using $d_B1$ and $d_B2$, and the type of edge is determined based on the comparison of the peak widths. Since it is considered that the peak width of the edge formed facing the core gap 1202 is narrower than the peak width of the edge formed facing the spacer gap 1203, it is possible to specify the edge formed on the core gap side and the edge formed on the spacer gap side by the comparison of the peak widths. For example, in a case where the width of the core gap is measured, it is possible to execute measurement after a desired object to be measured is accurately specified by executing the measurement based on the above specification. Since the edges formed on the core gap side and the edges framed on the spacer gap side appear alternately two by two, it is possible to identify edges and patterns while suppressing the influence of noise and the like, by performing addition averaging for each type.

In the example described above, although an example in which the edge and the pattern are determined after the peak width without the influence of the charging is theoretically calculated by extrapolation is described, for example, in the case where there is a predetermined relationship between the differences ($\Delta d_A$, $\Delta d_B 1$) in peak widths obtained with two or more landing energies or the inclination ($\Delta d_A/(V_2-V_1)$, ($\Delta d_B/(V_2-V_1)$)) of the function obtained based on the measurement results of two peak widths, it is possible to identify the edges and the like by using the relationship. For example, when it is known in advance that $\Delta d$ of the spacer gap is larger than $\Delta d$ of the core gap, it is possible to perform automatic identification and automatic measurement of the pattern using the obtained electron microscopic image by preparing an algorithm that determines an edge having the larger difference in peak width as the edge facing the spacer gap and determines an region surrounded by the edges as the spacer gap.

According to the embodiment described above, even if there is a slight difference on the image, it is possible to perform highly accurate measurement based on accurate identification of patterns and edges and accurate identification of objects to be measured by changing the landing energy and making the difference obvious. Even if there is a slight difference on one SEM image, since the difference can be clarified by changing the landing energy, it becomes possible to easily identify a pattern that is difficult to identify and specify an edge to be measured that is difficult to identify.

In the present embodiment, since the pattern and the edge are identified and measured using the index value (measurement value obtained when the landing energy obtained based on extrapolation is zero, a difference value, inclination, and the like calculated from a plurality of measurement values when the landing energy is changed to two or more) obtained from at least two measurement values obtained when the landing energy of the electron beam is changed, it is possible to perform more accurate measurement. In particular, the measurement value at the landing energy of zero obtained by extrapolation is a measurement result theoretically measured in a state where there is no scattering of the electron beam, and it is possible to perform highly accurate measurement without the influence of charging.

Further, a measurement value at a desired landing energy may be calculated by interpolation, instead of extrapolation. For example, a measurement result CDm obtained when the electron beam having the landing energy of Vm of which secondary electron emission efficiency δ (=the amount of electrons emitted from the sample/the amount of electrons incident on the sample) is 1.0 is scanned may be obtained from a measurement result CD1, which is obtained when the electron beam of the landing energy V1 (<Vm (for example, negatively charged electron beam)) is scanned, and a measurement result CDn, which is obtained when the electron beam of the landing energy Vn (>Vm (for example, positively charged electron beam)) is scanned. The fact that the secondary electron emission efficiency δ is 1.0 indicates that the negative charge incident on the sample and the negative charge emitted are in the same state, and it is a state in which charging is not caused by irradiation with an electron beam. It is possible to obtain the measurement result, which is obtained when such an electron beam is scanned, by interpolation of two or more measurement results obtained using at least two different landing energies. This method is particularly effective in a case where in some circumstances, it is not possible to use an electron beam having the landing energy of Vm and when measurement using election beams of V1 and Vn is possible.

Furthermore, in the example described above, although an example in which a plurality of measurements are executed by the scanning with electron beams of different landing energies with respect to the same pattern edge (same field of view position) and the measurement value estimation by extrapolation or interpolation is performed after execution of the measurement, if the composition and structure are the same, the measurement may be performed by changing the visual field position (edge to be measured) even in a different pattern or position.

<Cooperation with Design Data>

Figure 10:
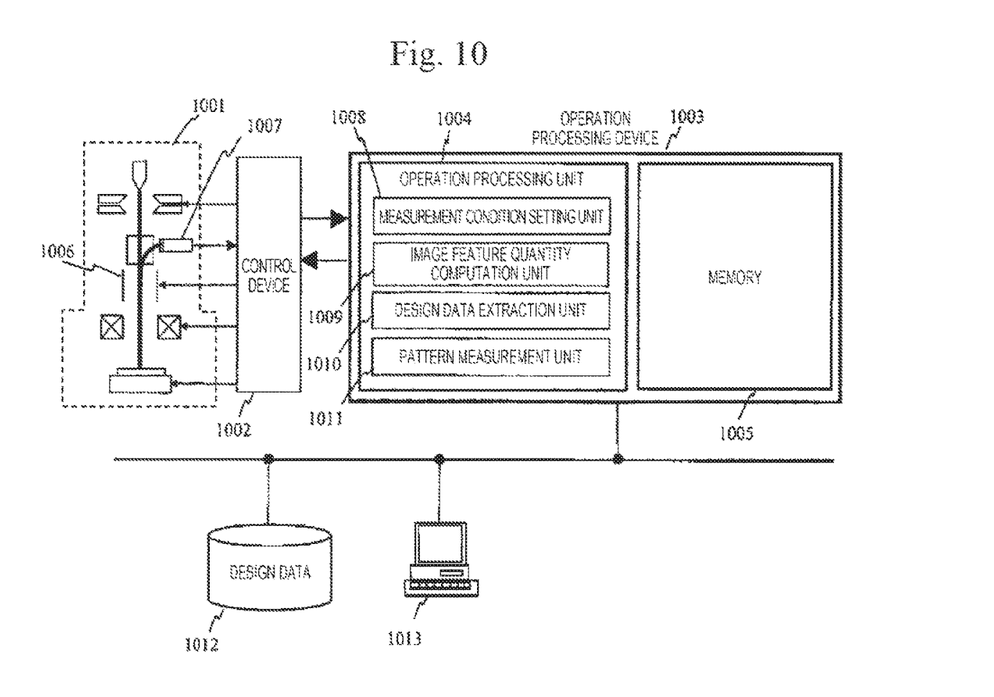
FIG. 10 is a diagram illustrating an example of a semiconductor measurement system including a scanning electron microscope.

The control device of the scanning electron microscope controls each configuration of the scanning electron microscope and also has a function of forming an image based on the detected electrons and a function of deriving a feature point such as a taper or a round based on intensity distribution of the detected electrons. FIG. 10 illustrates an example of a pattern measurement system including an operation processing device 1003.

This system includes a scanning electron microscope system constituted with an SEM main body 1001, a control device 1002 of the SEM main body, and the operation processing device 1003. In the operation processing device 1003, an operation processing unit 1004 which supplies a predetermined control signal to the control device 1002 and executes signal processing of the signal obtained by the SEM main body 1001, and a memory 1005 for storing obtained image information and recipe information are built in. In the present embodiment, the control device 1002 and the operation processing device 1003 are described as separate entities, but may be an integrated control device.

Electrons emitted from the sample or electrons generated in the conversion electrode by the beam scanning by a deflector 1006 are captured by a detector 1007 and converted into digital signals by an A/D converter built in the control device 1002. Image processing according to the purpose is performed by image processing hardware such as a CPU, ASIC, and FPGA built in the operation processing device 1003.

In the operation processing unit 1004, a measurement condition setting unit 1008 for setting measurement conditions such as scanning conditions of the deflector 1006 based on measurement conditions and the like input by an input device 913 and an image feature quantity computation unit 1009 for obtaining a profile in a region of interest (ROI) input by the input device 1013 from the obtained image data are built in. In the operation processing unit 1004, a design data extraction unit 1010 that reads design data from a design data storage medium 1012 according to the conditions input by the input device 1013 and converts the design data, from vector data to layout data as needed is also built in. A pattern measurement unit 1011 for measuring dimension of the taper and round of the pattern based on the acquired signal waveform is built therein. In the pattern measurement unit 1011, measurement of dt and dr with respect to the ROI profile obtained by the image feature quantity computation unit 1009 is conducted, and dt and dr at acceleration of 0 V are obtained by extrapolation. Furthermore, on a display device provided in the input device 1013 connected to the operation processing device 1003 via a network, a GUI for displaying an image, an inspection result, and the like to the operator is displayed. For example, it is also possible to superimpose image data, design data and observation results which are information of the taper and the round to be displayed as a map.

It is also possible to perform processing or control by allocating some or control and processing in the operation processing device 1003 to a CPU, a computer or the like installed with a memory capable of storing images, and the like. The control device 1002 and the operation processing device 1003 may be configured as one operation device. The input device 1013 also functions as an imaging recipe creation device that sets the measurement conditions including the coordinates of an electronic device required for inspection and the like, a type of the pattern, a photographing condition (optical condition and stage movement condition) as an imaging recipe. The input device 1013 also has a function of collating input coordinate information and information on the type of pattern with layer information of design data and pattern identification information and reading required information from the design data storage medium 1012.

The design data stored in the design data storage medium 1012 is represented in a GDS format, an OASIS format or the like, and is stored in a predetermined format. The design data may be of any type as long as software for displaying the design data can display format of the design data and can handle the design data as graphic data. The graphic data may be line segment image information subjected to deformation processing so as to be close to the actual pattern by conducting exposure simulation, instead of line segment image information indicating an ideal shape of a pattern formed based on design data.

The measurement condition setting unit 1008 sets observation conditions to be set by the steps illustrated in FIG. 5. For example, the operation condition of the device is automatically set by setting the size of the FOV, the position (coordinates) of the FOV, the size of the ROI, and the position of the ROI in layout data in the vicinity of the measurement target pattern extracted by the design data extraction unit 1010, by using the input device 1013. The design data extraction unit 1010 reads the design data from the design data storage medium 1012 according to the conditions input by the input device 1013 and converts the design data from vector data to the layout data as necessary, so that the FOV and the ROI can be set on the layout data.

Figure 11:
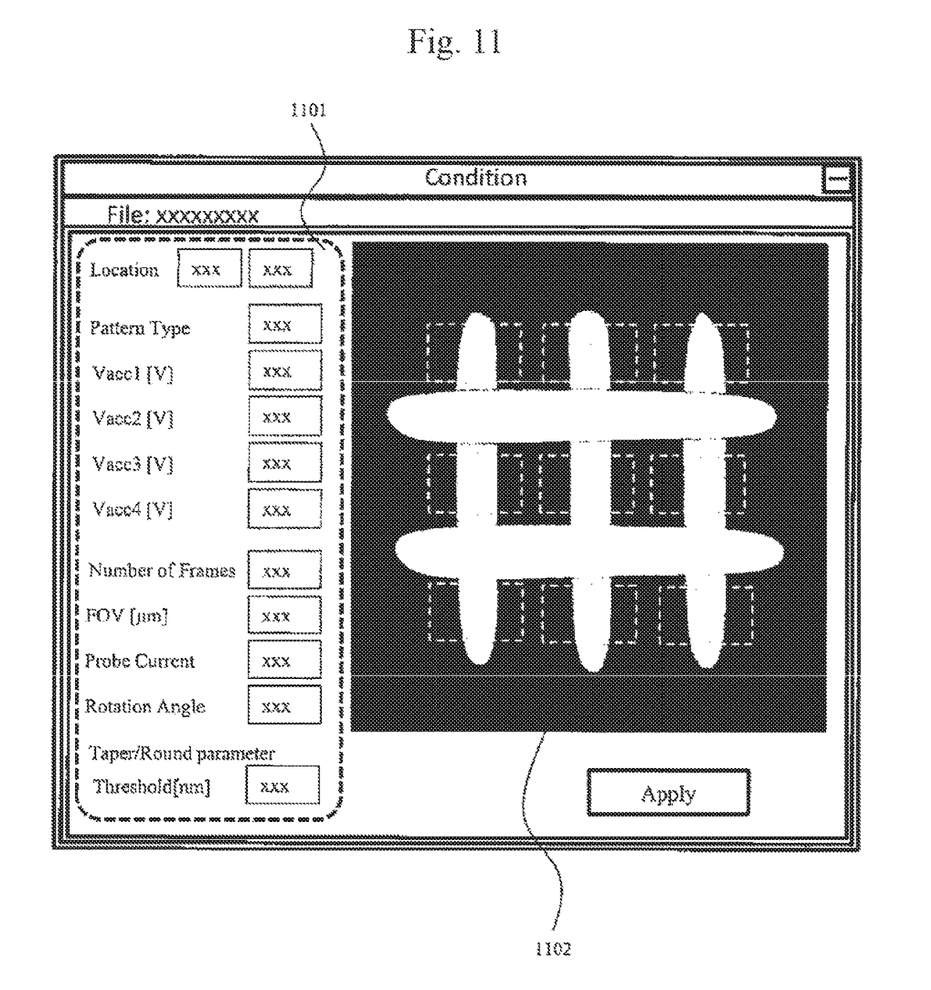
FIG. 11 is a diagram illustrating an example of a graphical user interface (GUI) screen for setting an operation condition of a SEM.

FIG. 11 is a diagram illustrating an example of a GUI screen for, setting operation conditions of the SEM. Designation of the ROI is performed on an image (or layout data) acquired in advance. The ROI is set by designating any two-dimensional region on the image 1102 with a mouse or the like. In particular, the GUI screen illustrated in FIG. 11 is provided with voltage (Vacc) setting window 1101 for setting a plurality of acceleration conditions. In the example of FIG. 11, it is possible to set threshold values when dividing Location (coordinate), Pattern Type (type of a pattern), Vacc (beam acceleration voltage), Number of Frames (number of integrated frames), FOV (magnitude of FOV), Probe Current (beam current), Rotation Angle (scanning direction), the taper, and the round.

REFERENCE SIGNS LIST

1: electron source
2: electron beam
3: capacitor lens
4: deflector
5: objective lens
6: sample
7: secondary electron
8: detector
1001: SEM main body
1002: control device
1003: operation processing device
1004: operation processing unit
1005: memory
1006: deflector
1007: detector
1008: measurement condition setting unit
1009: image feature quantity computation unit
1010: design data extraction unit
1011: pattern measurement unit
1012: design data storage medium
1013: input device
1101: observation condition setting window
1102: ROI specification region

The invention claimed is:
1. A charged particle beam device which includes scanning deflector for a scanning with a charged particle beam emitted from a charged particle source, a detector for detecting the charged particle obtained based on the scan- ning with the charged particle beam with respect to a sample, and a computation device for generating a signal waveform based an on output of the detector and computing a pattern dimension formed on the sample by using the signal waveform, wherein the computation device calculates an index value relating to a pattern formed on the sample from at least a first measurement result obtained by the scanning with the charged particle beam having first landing energy and a second measurement result obtained by the scanning with the charged particle beam having second landing energy.

2. The charged particle beam device according to claim 1, wherein the first measurement result and the second measurement result are dimensional values relating to the pattern and the computation unit calculates an edge dimension value at third landing energy other than the first landing energy and the second landing energy by extrapolation.

3. The charged particle beam device according to claim 2, wherein the third landing energy is zero.

4. The charged particle beam device according to claim 1, wherein the first measurement result and the second measurement result are obtained based on a width of a peak of the signal waveform.

5. The charged particle beam device according to claim 4, wherein the first measurement result and the second measurement result are dimensional values relating to a taper of the pattern.

6. The charged particle beam device according to claim 1, wherein the computation device estimates a taper angle of the pattern from change in a position of a bottom end of the pattern when scanning is performed with different landing energies.

7. The charged particle beam device according to claim 1, wherein the computation device displays a taper distance and a round region of the pattern obtained based on extrapolation of the first measurement result and the second measurement result as a three-dimensional structure.

8. The charged particle beam device according to claim 7, wherein the computation device displays a taper amount and a round amount of a pattern included in an image in a map form on a display device.

9. The charged particle beam device according to claim 7, wherein the computation device estimates height information of the pattern from a signal amount of the bottom of the pattern and estimates and displays the three-dimensional structure in combination with a taper shape and a round shape of the pattern.

10. The charged particle beam device according to claim 1, wherein the computation device identifies the pattern or a type of an edge of the pattern based on the index value.

11. A charged particle beam device which includes a charged particle source, a deflector for a scanning with a charged particle beam emitted from the charged particle source onto a sample, a detector for detecting electrons emitted from the sample by the scanning with the charged particle beam with respect to the sample, an image memory for storing a signal obtained in the detector, a control device for controlling the deflector, the charged particle beam device comprising:

a computation device for measuring a dimension of a pattern formed on a sample based on irradiation of the charged particle beam, wherein the computation device obtains a first distance between a peak and a bottom of a first signal waveform obtained based on irradiation with a charged particle beam, having a first landing energy and a second distance between a peak and a bottom of a second signal waveform obtained based on irradiation with a charged particle beam having a second landing energy different from the first landing energy and obtains a distance between the peak and the bottom at a landing energy different from the first and second landing energies based on extrapolation of the first distance and the second distance.

12. A pattern measurement device and a program which includes a computation device for generating a signal waveform based on a detection signal obtained by a charged particle beam device and calculating the dimension of a pattern formed on a sample using the signal waveform, wherein the computation device calculates an index value relating to the pattern formed on the sample at least from a first measurement result obtained by a scanning with the charged particle beam having first landing energy and a second measurement result obtained by the scanning with the charged particle beam having second landing energy.

* * * * *